United States Patent [19]

Maeke et al.

[11] 4,163,017

[45] Jul. 31, 1979

[54] HIGH PURITY CHENODEOXYCHOLIC ACID AND METHOD FOR OBTAINING SAME

[75] Inventors: Siegfried Maeke, Kirchdorf; Paul Rambacher, Rosenheim-Mitterfeld, both of Fed. Rep. of Germany

[73] Assignee: Diamalt Aktiengesellschaft, Fed. Rep. of Germany

[21] Appl. No.: 782,080

[22] Filed: Mar. 28, 1977

[30] Foreign Application Priority Data

Mar. 29, 1976 [DE] Fed. Rep. of Germany ....... 2613346

[51] Int. Cl.$^2$ ............................................. C07J 9/00
[52] U.S. Cl. ................................................. 260/397.1
[58] Field of Search ...................................... 260/397.1

[56] References Cited

U.S. PATENT DOCUMENTS

| | | | |
|---|---|---|---|
| 3,965,131 | 6/1976 | Wiele et al. | 260/397.1 |
| 4,022,806 | 5/1977 | Frost et al. | 260/397.1 |

OTHER PUBLICATIONS

The Lancet (1974), p. 1518 an article by Straelen et al.

*Primary Examiner*—Elbert L. Roberts
*Attorney, Agent, or Firm*—Roylance, Abrams, Berdo & Kaul

[57] ABSTRACT

Chenodeoxycholic acid melting in the range of 168°–171° C. and of such high purity as to be suitable for human therapeutic use is obtained by crystallization from acetonitrile.

5 Claims, 2 Drawing Figures

HIGH PURITY CHENODEOXYCHOLIC ACID AND METHOD FOR OBTAINING SAME

This invention relates to chenodeoxycholic acid (3α,7α-dihydroxy-5β-cholanic acid) of such high purity as to be suitable for human therapeutic use, and to methods for obtaining the high purity product.

BACKGROUND OF THE INVENTION

Chenodeoxycholic acid is one of the acids occurring naturally in the bile of humans and other warm blooded animals. Chenodeoxycholic acid in forms heretofore obtainable is known to dissolve gallstones, which consist of cholesterol, and has therefore been recognized as an important compound in human medicine. However, to be suitable for human therapeutic use, chenodeoxycholic acid must be available in very pure form. Human therapy, as in treatment for gallstones, requires that the compound be administered over protracted time periods, and presence of even small impurities, or of an inhomogeneity of the active compound, may lead to undesirable side effects and the symptoms accompanying the side effects. For example, liver toxicity has been observed as a result of lithocholic acid, which can occur as an impurity in chenodeoxycholic acid preparations of the prior art.

Chenodeoxycholic acid has been produced from natural starting materials. Thus, the cholic acid is esterified in the cholic acid fraction of the gall, the 3- and 7-hydroxy groups are then partially acetylated, and the free 12-hydroxy group is oxidized with chromic acid to the keto group. The 12-keto compound is heated over an extended period to temperatures of about 200° C. in the presence of hydrazine hydrate and potassium hydroxide in ethylene glycol. So produced, the crude chenodeoxycholic acid contains a number of by-products which can be separated only with great difficulty, and the ultimate product exhibits an amorphous glass-like condition so as to be very difficult to crystallize.

Attempts to purify the crude chenodeoxycholic acid material by chromatographic procedures, via the methyl ester with ethyl acetate-benzene mixtures as eluents, have been reported (*Acta Chemica Scandinavica* 17, 1963, pages 173-186). Purification has also been attempted by way of production and isolation of the sodium salt, conversion of the salt into the acid, and subsequent recrystallization from ethyl acetate-heptane (*J. Am. Chem. Soc.* 72, 1950, page 5530). But both procedures lead to poor yields of products of low purity.

West German patent application No. (OS) 2,302,744 describes an attempted purification in which the raw chenodeoxycholic acid is treated in methanolic solution with a calcium or strontium salt, the corresponding chenodeoxycholic acid salt being precipitated. After separation, the salt is acidified and the chenodeoxycholic acid product extracted. There, purity of the product was characterized chromatographically and no melting point is reported. West German Pat. No. 2,404,102 describes the purification of crude chenodeoxycholic acid in the form of its aqueous alkali salt, preferably the sodium or potassium salt, which is treated with an organic solvent, preferably ethyl acetate or a mixture of isobutanol and toluene, and the salt solution is then acidified with a dilute acid, preferably hydrochloric acid, then extracted, and the chenodeoxycholic acid product is then precipitated with water. The product is reported to have a melting range of 143°-146° C.

It has been postulated (*The Lancet*, 1974, page 1518) that a very pure chenodeoxycholic acid will exhibit a melting point of 168° C., but no way to produce such a material and no further criteria for its characterization have been disclosed.

X-ray investigations of the structures for the chenodeoxycholic acid substances heretofore described have shown that the products are either X-ray-amorphous or else merely have microcrystalline partial areas which do not produce and characteristic X-ray diffraction spectra. Thus, none of the prior-art products have been of the high purity necessary for human therapeutic use, and there has been a critical continuing need for such a product.

OBJECTS OF THE INVENTION

It is accordingly a general object to obtain, as a new product suitable for human therapeutic usage, a chenodeoxycholic acid of very high purity.

Another object is to devise a method by which such a high purity product can be obtained, with the method being technically easily carried out, and with the chenodeoxycholic acid product being essentially free of other bile acids and being characterized unambiguously by its crystal structure, melting range and infrared absorption characteristics.

SUMMARY OF THE INVENTION

The invention stems from the surprising discovery that, despite lack of success in prior-art attempts to obtain pure chenodeoxycholic acid by recrystallization from many customary solvents, the pure product can be obtained by crystallization from acetonitrile, the recovered product having a melting range of 168°-171° C., a clear and characteristic X-ray spectrum and thus a definite crystalline structure, and a characteristic infrared absorption spectrum.

DETAILED DESCRIPTION OF THE PRODUCT

Figure 1:
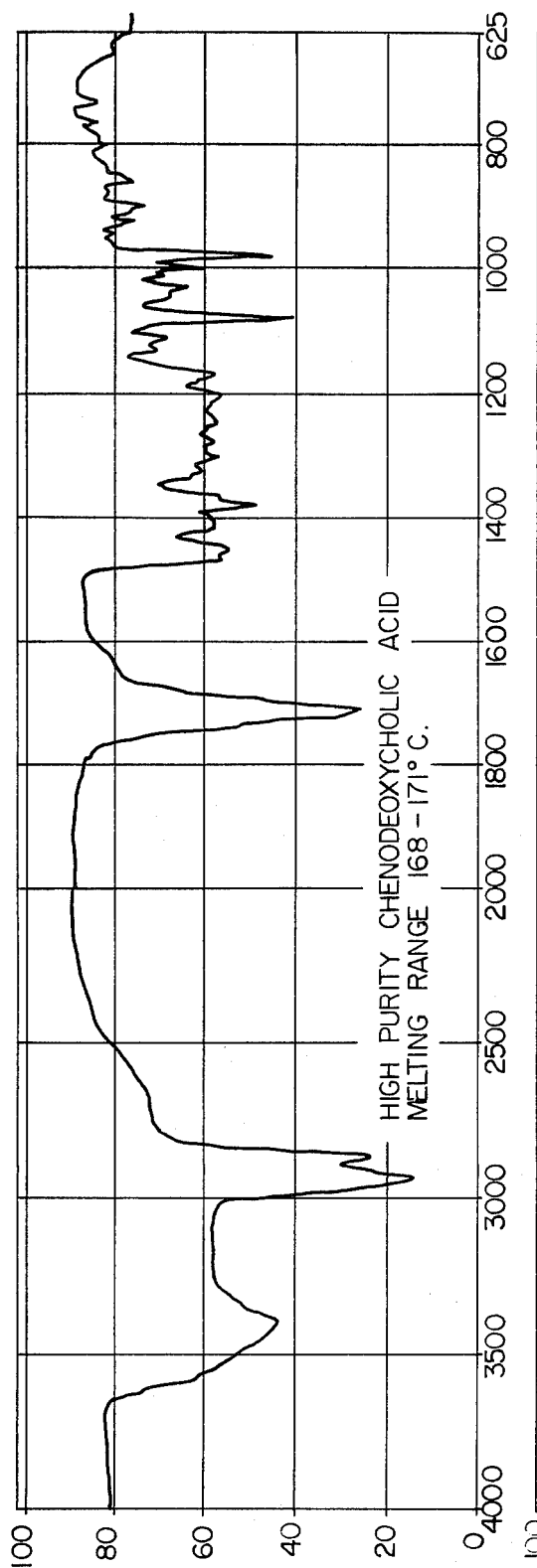

The product embodiment of the invention is chenodeoxycholic acid in a highly purified state heretofore unreported. Chenodeoxycholic acid according to the invention is in monoclinic crystalline form, the crystals being flat prisms or needles with blunted edges. By X-ray determination, the crystal lattice parameters are as follows:
$a = 19.1 \pm 0.29$ Å
$b = 8.21 \pm 0.12$ Å
$c = 15.1 \pm 0.22$ Å
$\beta = 100° \pm 1.5°$ The crystalline material melts in the range 168°-171° C., and has a clear X-ray spectrum. The chenodeoxycholic acid of the invention exhibits the characteristic infrared absorption spectrum shown in FIG. 1, such spectrum being observably distinct from that, seen in FIG. 2, for the typical prior art "purified" chenodeoxycholic acid which melts in the range 126°-129° C.

DETAILED DESCRIPTION OF THE METHOD

Method embodiments of the invention employ as a solvent a liquid comprising acetonitrile and not more than 10% by weight water. Thus, the solvent can consist of 100-90% by weight acetonitrile and, correspondingly, 0-10% water, with 98-96% acetonitrile and 2-4% water being preferable. The solvent can carry a conventional filter aid such as diatomaceous earth or activated charcoal.

The solvent is employed in an amount such that the weight ratio of the solvent to the crude chenodeoxycholic acid is from 8:1 to 40:1, with the narrower range of 10:1 to 15:1 being especially advantageous.

In dissolving the crude chenodeoxycholic acid, the solvent is heated to a temperature well above the crystallization temperature of the product to assure good dissolution. Thus, the crude material can be introduced into the solvent liquid and the liquid heated to, e.g., 75°–80° C. when the solvent contains no water and 85°–90° C. when the solvent contains 2–4% water, while agitating the solution. If a filter aid has been employed, the filter aid is removed and the liquid filtrate then cooled slowly, with agitation, to at least 18° C. to effect crystalization of the product. The crystals are then recovered, as by centrifuging, washed with acetonitrile, then washed again with water, and finally dried under vacuum. The upper heating temperature limit is defined by the boiling temperature of the solvent liquid or of the solvent liquid composition respectively.

The method can be carried out to recover the high purity product of the invention by commencing with a solution of an alkali salt of the crude chenodeoxycholic acid, the solution being prepared in a known manner. The solution is treated with an acid, preferably hydrochloric acid, to cause the raw chenodeoxycholic acid to precipitate, and the precipitate is recovered and dried. The dried precipitate is then dissolved in acetonitrile containing 0–10%, preferably 2–4% by weight water, and the high purity chenodeoxypholic acid of the invention is then obtained by recrystallization as described above. This product thus recovered melts in the range 168°–171° C., exhibits the crystallographic data hereinbefore specified, and has the characteristic infrared absorption spectrum seen in FIG. 1.

The following examples are illustrative:

EXAMPLE 1

To 1400 ml. of an approximately 50% water/triglycol solution of the potassium salt of chenodeoxycholic acid, obtained by the Wolff-Kishner reduction from 50 g. of 7-acetyl-12-ketochenodeoxycholic acid, 220 ml. of dilute hydrochloric acid is added to bring the pH to 2. The solution is stirred and the crude chenodeoxycholic acid precipitates. The precipitate is recovered and dried to constant weight at about 60° C. About 36 g. of the crude chenodeoxycholic acid, melting in the range 126°–129° C., is obtained.

Figure 2:
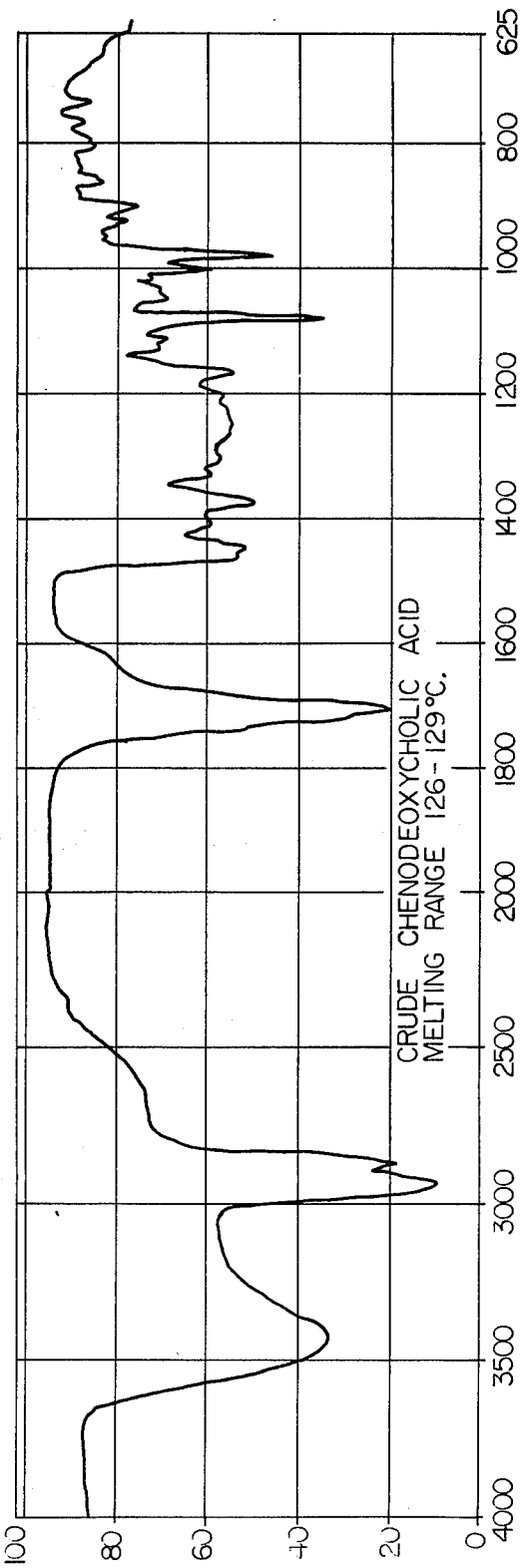

Twenty five grams of crude chenodeoxycholic acid so obtained is dissolved in 750 ml. of acetonitile while stirring and heating. 3 g. of activated charcoal is added and then removed by suction filtering. The resulting liquid filtrate is cooled, the pure chemodeoxycholic acid crystallizing out. The crystals are recovered by suction filtering and the recovered crystals dried under vacuum. The yield is 19 g. of pure chenodeoxycholic acid with a melting range of 168–171° C. and exhibiting an infrared absorption spectrum as shown in FIG. 1. The product has a monoclinic crystallographic system with the lattice parameters hereinbefore specified.

EXAMPLE 2

Twenty five hundred liters of product obtained by Wolff-Kishner reduction from 90 kg. of 7-acetyl-12-ketochenodeoxycholic acid is combined with 370 l. of dilute hydrochloric acid with vigorous stirring and mild heat, with an end pH of about 2, the potassium salt of chenodeoxycholic acid precipitating out. The precipitate is recovered by centrifuging and is dried, yielding about 150 kg. of crude chenodeoxycholic acid melting at 126°–129° C.

One hundred and fifty kilograms of crude chenodeoxycholic acid thus obtained is introduced with stirring into a solvent liquid made up of 1700 liters of acetonitrile and 40 liters of water. Dissolution of the crude chenodeoxycholic acid is accomplished with heating and agitation, and 5 kg. of diatomaceous earth is then added, heating then being continued to bring the solution to 85°–90° C. The diatomaceous earth is then filtered out conventionally. The resulting liquid filtrate is cooled to at least 18° C. while stirring. The crystallized pure chenodeoxycholic acid is recovered by centrifuging, washed with acetonitrile, then washed with water and dried under vacuum. The yield is about 120 kg. of pure chenodeoxycholic acid melting in the range 168–171° C., exhibiting the infrared absorption spectrum shown in FIG. 1, and the crystallographic data hereinbefore specified.

What is claimed is:

1. The method for producing chenodeoxycholic acid suitable for human therapeutic use, characterized by a monoclinic crystallographic system with the lattice parameters $a = 19.1 \pm 0.29$ Å
   $b = 8.21 \pm 0.12$ Å
   $c = 15.1 \pm 0.22$ Å
   $\beta = 100° \pm 1.5°$;

the crystals being in the form of relatively flat prisms or needles with blunted edges; a melting range of 168°–171° C.; and an infrared absorption spectrum essentially as shown in FIG. 1, which method comprises dissolving a crude chenodeoxycholic acid in acetonitrile containing 0–10% water at a temperature substantially above 18° C. to form a solution in which the weight ratio of solvent to crude chenodeoxycholic acid is from about 8:1 to about 40:1; cooling said solution to at least 18° C. but above the freezing point of the solution and thereby causing the pure chenodeoxycholic acid to precipitate in crystalline form; and recovering the crystalline product.

2. The method defined in claim 1, wherein said solvent comprises 2–4% water.

3. The method defined in claim 1, wherein said ratio is from 10:1 to 15:1.

4. The method defined in claim 1, wherein said step of dissolving the crude chenodeoxycholic acid comprises heating the solution to 75°–90° C.

5. The method defined in claim 1, wherein said step of dissolving the crude chenodeoxycholic acid comprises adding to the solvent a finely divided filter aid, said filter aid being removed from the solution before said step of cooling the solution.

* * * * *